United States Patent
Murphy et al.

(10) Patent No.: US 7,348,019 B1
(45) Date of Patent: *Mar. 25, 2008

(54) STABILIZED BLOCK PESTICIDE COMPOSITIONS

(75) Inventors: Dennis Lee Murphy, Flower Mound, TX (US); Jeanne Ann Witte, Carrollton, TX (US); Kim W. Yang, Dallas, TX (US)

(73) Assignee: Wellmark International, Schaumburg, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/461,403

(22) Filed: Jul. 31, 2006

Related U.S. Application Data (63) Continuation-in-part of application No. 10/794,849, filed on Mar. 4, 2004.

(51) Int. Cl.
*A01N 25/32* (2006.01)
(52) U.S. Cl. ............ 424/410; 424/438; 424/442; 426/53; 426/807; 514/549
(58) Field of Classification Search ............ None
See application file for complete search history.

(56) References Cited

U.S. PATENT DOCUMENTS

| | | | |
|---|---|---|---|
| 4,383,391 A | 5/1983 | Thomas et al. | |
| 4,732,762 A | 3/1988 | Sjogren | |
| 4,876,091 A | 10/1989 | Clarke, Jr. | |
| 5,096,710 A | 3/1992 | Minagawa et al. | |
| 6,001,382 A | 12/1999 | Levy | |
| 6,613,138 B2 | 9/2003 | Welshimer et al. | |
| 6,864,256 B2 | 3/2005 | Palma | |
| 2002/0010156 A1 | 1/2002 | Kennedy et al. | |
| 2006/0127531 A1* | 6/2006 | Jobe et al. | 426/2 |

FOREIGN PATENT DOCUMENTS

CS 258918 * 4/1989

OTHER PUBLICATIONS

HCAPLUS# 112:93954, Hrdy et al in CS 258918 Sep. 16, 1988. bait insecticide for ant—abstract.*
Morrison—Feeds & Feeding PPP 528-536☐☐☐☐1957.*
Moon et al , Intake & Efficacy of Methoprene & Stirofos Mineral Blocks—pp. 1738-1745, Journal of Economic Entomology—vol. 86, # 6, 1993.*
Product label for VIGORTONE, FC No. 32S Plus IGR; manufactured by North American Nutrition Companies, Inc.
Product label for Moorman's IGR Mineral Block; manufactured by Moorman Mfg. Co.

* cited by examiner

*Primary Examiner*—Neil S. Levy
(74) *Attorney, Agent, or Firm*—Townsend and Townsend and Crew LLP (57) ABSTRACT

The present invention provides a solid block formulation, and methods of making and methods of use. In addition, methods of controlling insects on cattle are also provided.

41 Claims, 9 Drawing Sheets

FIG. 1

EXCELLENT

GOOD

AVERAGE TO BELOW

UNACCEPTABLE

STABILIZED BLOCK PESTICIDE COMPOSITIONS

CROSS-REFERENCE TO RELATED APPLICATIONS

The present application is a continuation-in-part application of, and claims priority to, U.S. patent application Ser. No. 10/794,849, filed Mar. 4, 2004, allowed, the teachings of which are hereby incorporated by reference in their entirety for all purposes.

BACKGROUND OF THE INVENTION

Scientists estimate that horn flies (*Haematobia irritans*) cost U.S. cattle producers $876 million each year. Together with fire ants and nuisance flies, they have a tremendously negative impact on the profits of farmers and ranchers in every industry.

Infestation occurs rapidly with 1000-4000 flies per animal in an untreated herd. In general, horn flies congregate on the back and shoulders of cattle, and tend to rest quietly on the host. Horn flies rarely leave their host, except to lay eggs, change host animals or remain outdoors when the host moves indoors.

Because they are a nuisance to the cattle, horn flies interrupt grazing patterns. The cattle tend to waste energy and even go off their feed. Due to horn flies infestations, calves are lighter at weaning by about 10-25 pounds. In addition, a 14% weight loss over 120 day fly period can amount to 26 lbs. per head. In the summer season, horn flies can cause 15-50 lbs. loss per head. At $0.90 per lb., a 30 lb. weight loss equals a $27.00 loss per head. Moreover, cows can go out of condition during breeding.

In view of the foregoing, there is a need for new more effective pesticide formulations and methods to control and treat flies, such as horn fly infestations in cattle. The present invention satisfies these and other needs.

SUMMARY OF THE INVENTION

The present invention provides inter alia, pesticide formulations used to control and treat fly infestation in cattle. Advantageously, the pesticide formulations have increased shelf-life. In fact, the pesticide formulations of the present invention prolong the shelf-life many fold. As such, the present invention provides a solid shelf-life extending pesticide formulation, comprising: a) methoprene on a solid carrier, wherein the solid carrier is selected from the group of silica gel and charcoal; and b) molasses, wherein the solid formulation is formulated as a feed-through animal product wherein the ratio of the molasses to the methoprene is about 100,000:1 w/w to about 2:1 w/w.

In still another embodiment, the present invention provides a method for producing a shelf-life extending pesticide formulation, comprising: a) providing a pesticide formulation; b) providing a shelf-life extending agent to produce an admixture; and c) processing the admixture to produce a solid formulation.

In another embodiment, the present invention provides a solid shelf-life extending pesticide formulation, comprising: a) methoprene sprayed on dry molasses; and b) a molasses binder, wherein the solid formulation is formulated as a feed-through animal product having a ratio of the molasses to methoprene is about 100,000:1 w/w to about 2:1 w/w.

In still yet another embodiment, the present invention provides a method for controlling an insect on cattle, comprising: administering a solid pesticide formulation as a feed-through product to cattle, wherein the solid formulation is formulated into a block; and allowing the feed-through product to pass through the cattle into manure, wherein the pesticide formulation is released in the manure to control the insect.

Advantageously, the present invention greatly improves the shelf-life of pesticides such as insect growth regulators in animal mineral feeds. Prior to the advent of the present invention, shelf-stability and shelf-life longevity was short. The present invention prolongs the shelf-life many fold. In addition, other advantages of the formulations of the present invention include reducing dustiness, reducing the electrostatic tendency of the final product, controlling the particle size during manufacture, taste masking, and decreased environmental toxicity for feed mill workers. These and other objects, embodiments and advantages will become more apparent when read with the drawings and detailed description which follow.

BRIEF DESCRIPTION OF THE DRAWINGS

FIG. 2 shows a schematic of various degrees of horn fly infestation on cattle.

DETAILED DESCRIPTION OF THE INVENTION

I. General

The present invention provides pesticide formulations, methods of making pesticide formulations and methods of treating animals using the new pesticide formulations. The pesticide formulations have increased shelf-life. Advantageously, in certain aspects, the pesticide formulations of the present invention can be used in feed-through products to treat and control insect infestation in cattle. Various insects can be controlled and treated using the formulations and methods of the present invention. These include, but are not limited to, face flies, house flies, stable flies and horn flies. Horn flies are especially susceptible to the formulations and methods of the present invention.

II. Pesticides

Various pesticides can be used in the present invention. In a preferred aspect, the pesticide of the present invention is an insect growth regulator (IGR). Insect growth regulators (including juvenile hormones) are well known for their use and efficacy in controlling or eliminating insect infestation in humans, in animals, and in both residential and industrial environments. Many types of insects are controllable by insect growth regulators, including flies (e.g., face flies, house flies, stable flies and horn flies), fleas, mosquitoes, flour beetles, cigarette beetles, and cockroaches. The regulators vary widely in chemical composition, and two of the more prominent classes are 2,4-dienoic acids and phenoxyphenoxy compounds, particularly phenoxyphenoxyalkoxyheterocyclics, as well as benzoylureas and triazine derivatives. Examples of 2,4-dienoic acids and related compounds are methoprene, hydroprene, neotenin, and epiphenonane. As used herein, "methoprene" includes R-methoprene, S-methoprene and mixtures of R and S methoprene. S-methoprene is the preferred methoprene. Examples of phenoxyphenoxy compounds are fenoxycarb and pyriproxyfen. Examples of benzoylureas are lufenuron, diflubenzuron, terflubenzuron, triflumaron, hexaflumaron, and flucycloxuron. An example of a triazine derivative is 2-cyclopropylamino-4,6-bis(dimethylamino)-s-triazine.

The following IGRs are suitable for the present invention. Chitin synthesis inhibitors are suitable such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, and triflumuron. In addition, juvenile hormone mimics are suitable such as epofenonane, fenoxycarb, hydroprene, kinoprene, methoprene, pyriproxyfen, and triprene. Further, juvenile hormones are suitable such as juvenile hormone I, juvenile hormone II, and juvenile hormone III. Other suitable IGRs include, molting hormone agonists, chromafenozide, halofenozide, and methoxyfenozide tebufenozide. Moreover, molting hormones such as α-ecdysone, and ecdysterone are suitable. In addition, molting inhibitors such as diofenolan and other IGRs, which include precocenes, such as precocene I, precocene II, and precocene III are suitable. Finally, unclassified insect growth regulators are suitable such as dicyclanil. Preferred IGRs include methoprene, hydroprene, kinoprene, fenoxycarb, pyriproxifen, and mixtures thereof. In the most preferred embodiment, methoprene is the IGR of choice.

A. Carriers

In certain aspects, the pesticide of the present invention comprises a carrier such as a solid carrier. Solid carriers, which may be used for dusts, wettable powders, water dispersible granules, or granules, may be mineral fillers, such as calcite, silica, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers include calcite or sand. Additionally, a multitude of pre-granulated inorganic or organic materials may be used, such as dolomite or crushed plant residues. Other suitable carriers include, but are not limited to, silica gel, sand, gypsum, charcoal, dry molasses and combinations thereof.

In certain aspects, the ratio of pesticide to carrier is about 0.001 to about 0.5 w/w. Preferably, the ratio of pesticide to solid carrier is about 0.01 w/w to about 0.1 w/w.

In certain aspects, the formulations of the present invention are solid formulations. Such solid formulations can be for example, a granule, a particle, a pellet, a capsule (e.g., a microcapsule), a tablet, a whole feed ration, and combinations thereof. In one embodiment, the solid formulation is about 50 μm to amount 5 mm in size. More preferably, the size is 0.2 mm to amount 2 mm in size such as 0.3, 0.4, 0.5, 0.6, 0.7, 0.8, 0.9, 1.0, 1.1, 1.2, 1.3, 1.4, 1.5, 1.6, 1.7, 1.8, 1.9 and 2.0 mm. In one particular aspect, the solids are homogenous granules, filtered through wire mesh, such as 16 mesh or 40 mesh.

In another embodiment, the formulation is formulated into a block or tub. The final form is about 1 liter to 250 liters in size, for example about 10 liters, 50 liters, 100 liters or about 150 liters. The weight of the formulation is about 1 kilogram to 250 kilograms such as 10 kg, 50 kg, 100 kg, or more than 150 kg.

B. Shelf-Life Extending Agent

In certain preferred aspects, the shelf-life extending agent is a carbohydrate (e.g. saccharide). Suitable carbohydrates include monosaccharides, oligosaccharides, polysaccharides and mixtures thereof. Suitable polysaccharides include, for example, a cyclodextrin, a starch, a carboxymethyl cellulose salt, an alginate, a methyl cellulose, an ethyl cellulose, a hydroxypropyl cellulose, sucrose, a starch glycolic acid salt, a molasses, lactose, dextrin, and distillers products such as distiller's grains and condensed distiller's solids. In certain aspects, the saccharide is a water soluble saccharide. In one preferred embodiment, the shelf-life extending agent is molasses. Suitable molasses includes, but is not limited to, beet sugar molasses, citrus molasses, hemicellulose extract, dried corn syrup, starch molasses, cane sugar molasses and combinations thereof. Those of skill in the art will know of other molasses suitable for use in the present invention.

In certain aspects, such as in a solid formulation, the ratio of the shelf-life extending agent to pesticide is about 100,000 to about 2:1, preferably, 40,000:1 to about 10,000:1, and more preferably, 5000:1 to about 2000:1 w/w.

In certain aspects, the shelf-life extending pesticide formulation further comprises a binding agent. Alternatively, the shelf-life extending agent is a binding agent.

In certain aspects, the shelf-life extending pesticide formulation further comprises a taste masking agent. Alternatively, the shelf-life extending agent is a taste masking agent.

In certain aspects, the formulations of the present invention further comprise an antioxidant. Suitable antioxidants include, but are not limited to, Vitamin E (including tocopherols and derivatives such as for example, α-tocopherol, α-tocopherol acetate, dl-α-tocopherol acetate, d-α-tocopherol acetate, tocopherols and the like), vitamin A palmitate, propyl gallate, butylated hydroxyanisole (BHA), butylated hydroxytoluene (BHT), and combinations thereof.

Surprisingly, the shelf-life extending agent such as molasses, will retard or prevent the adsorption of methoprene into/or by polymers and thermoplastics by methoprene. This advantageous property extends the shelf-life and broadens the variety of polymers and thermoplastics that can be used as packaging.

C. Minerals

In certain instances, the formulations of the present invention comprise elemental mineral(s) compounds. While a particular formulation commonly includes more than one of the elemental minerals and/or mineral compound, it need not and routinely does not include all of the mineral nutrients listed herein. The minerals include, but are not limited to, calcium (0.5% to 30%); phosphorous (0.3% to 16%); salt (sodium chloride) (0.2 to 80%); potassium (0.1 to 7.5%); magnesium (0.1 to 7.5%); zinc (200 to 25,000 mg/lb); iron (200 to 25,000 mg/lb); copper (30 to 85,000 mg/lb); cobalt (2 to 400 mg/lb); iodine (5 to 1500 mg/lb); manganese (200 to 25,000 mg/lb); and selenium (1 to 400 ppm). In one embodiment, the formulations of the present invention may include no more than about 5 wt. % of trace minerals.

The elemental minerals and/or mineral compounds can be provided using any of a number of mineral sources. These sources include, but are not limited to, calcium acetate, calcium carbonate, calcium chloride, calcium gluconate, calcium hydroxide, calcium iodate, calcium iodobehenate, calcium oxide, calcium sulfate (anhydrous or dihydrate), cobalt acetate, cobalt carbonate, cobalt chloride, cobalt oxide, cobalt sulfate, copper carbonate, copper chloride, copper gluconate, copper hydroxide, copper orthophosphate, copper oxide, copper pyrophosphate, copper sulfate, cuprous iodide, dicalcium phosphate, diiodosalicylic acid, disodium phosphate, ethylenediamine dihydroiodide, ferrous fumarate, iron ammonium citrate, iron carbonate, iron chloride, iron gluconate, iron oxide, iron phosphate, iron pyrophosphate, iron sulfate, reduced iron, magnesium acetate, magnesium carbonate, magnesium oxide, magnesium sulfate, manganese acetate, manganese carbonate, manganese chloride, manganese citrate (soluble), manganese gluconate, manganese orthophosphate, manganese oxide, manganese phosphate (dibasic), manganese sulfate, monocalcium phosphate, monosodium phosphate, potassium acetate, potassium bicarbonate, potassium carbonate, potassium chloride, potassium iodate, potassium iodide, potassium sulfate, sodium acetate, sodium chloride, sodium bicarbonate, sodium iodate, sodium iodide, sodium sulfate, sodium tripolyphosphate, sulfur, thymol iodide, tricalcium phosphate, zinc acetate, zinc carbonate, zinc chloride, zinc oxide, and zinc sulfate.

In one embodiment, the mineral includes a calcium source and salt (i.e., sodium chloride). In another embodiment, the mineral includes a source of at least one of calcium, sodium, potassium, phosphate, sulfur, or magnesium.

III. Methods of Making

In another embodiment, the present invention provides a method for producing a shelf-life extending pesticide formulation, comprising: a) providing a pesticide formulation; b) providing a shelf-life extending agent to produce an admixture; and c) processing the admixture to produce a solid form, wherein the solid formulation is about 50 µm to amount 5 mm in size. In certain aspects, the present invention improves the use of IGR methoprene granules to be used in other animal feed forms, such as loose minerals, pellets, cubes, complete feed ration blocks and tubs.

Advantageously, the present formulations and methods reduce the dustiness of the IGR product such as methoprene granules. This advantage improves protection of the IGR methoprene from reacting with other minerals and ingredients found in animal feeds. In addition, the electrostatic tendency of the methoprene granules can be greatly reduced using the formulations and methods of the present invention. Moreover, the safety for feed mill workers has been increased as the toxicity of the environment has been reduced.

Moreover, the formulations and methods improve the ease of use/control for feed mill workers since it is free-flowing. (non-electrostatic) and masks any unpleasant taste of the IGR in animal feeds.

In one embodiment, methoprene with or without an antioxidant is sprayed on a mixing powder bed of dry molasses or sugar or other carbohydrate, liquid molasses (sugar, carbohydrate) or syrup (molasses, sugar, carbohydrate) is followed as a binder, and the admixture is then granulated, dried, and screened through a standard sieve or perforated plate to a desirable granule size. The formulations and methods of the present invention greatly improves the stability of the IGR and provides a longer shelf life.

Moreover, the formulations and methods improve the particle size control of the IGR granules so tendency to segregate from the animal feed components is minimized which in turn, improves uniformity throughout the feed.

IV. Uses

Figure 1:
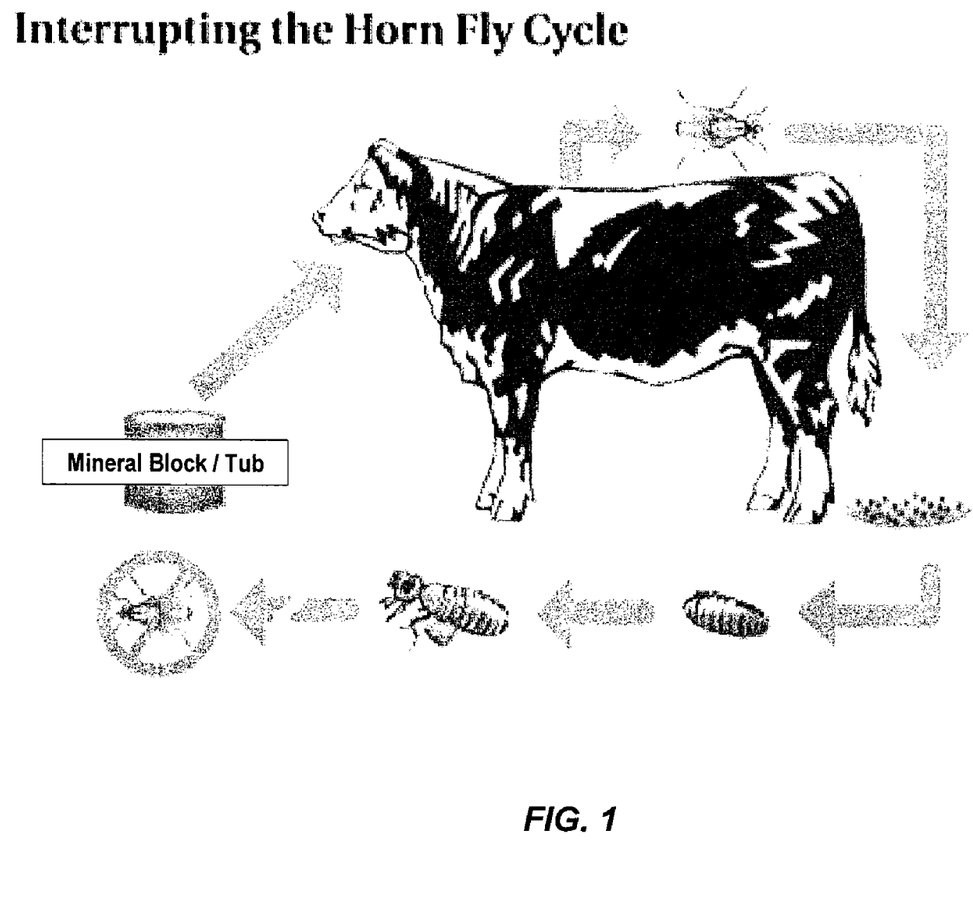
FIG. 1 shows a schematic of a use of the present invention.

In still other embodiments, the present invention provides a method for controlling or treating an insect on an animal such as cattle. As shown in FIG. 1, the method includes administering a pesticide formulation as a feed-through product to the animal, wherein the pesticide formulation is formulated into a final form such as a granule, a particle, a pellet, a capsule such as a microcapsule, a cube, a tablet such as a microtablet, a complete feed ration and combinations thereof. The feed-through product is allowed to pass through the animal into its manure. The pesticide formulation is released in the manure, thereby controlling the insect.

Turing now to FIG. 2, in one example, cattle are unacceptably infested with horn flies. Adult horn flies live 2 to 4 weeks taking 20 to 30 blood meals a day from the cattle. The pesticide formulation of the present invention is ingested with the cattle's mineral or feed. As they graze, cattle disperse the IGR via their manure. The compositions of the present invention breaks the life cycle of the horn fly, by for example, preventing pupae from molting into adults. In 1 to 2 days, eggs hatch into larvae. After 3 to 5 days, the larvae molt into pupae. Preferably, the composition of the present invention, such as an IGR composition, prevents adult emergence following pupal stage.

V. Examples

1. Example 1

This Example illustrates a storage stability study of five lots of 0.01% IGR mineral feed that were formulated with Altosid® (CP-10). These five lots (JM534, JM535, JM536, JM537, and JM538) do not comprise a shelf-life extending agent. Lot JM716 (Altosid® CP-2) is made in accordance to the present invention and comprises a shelf-life extending agent.

Figure 3:
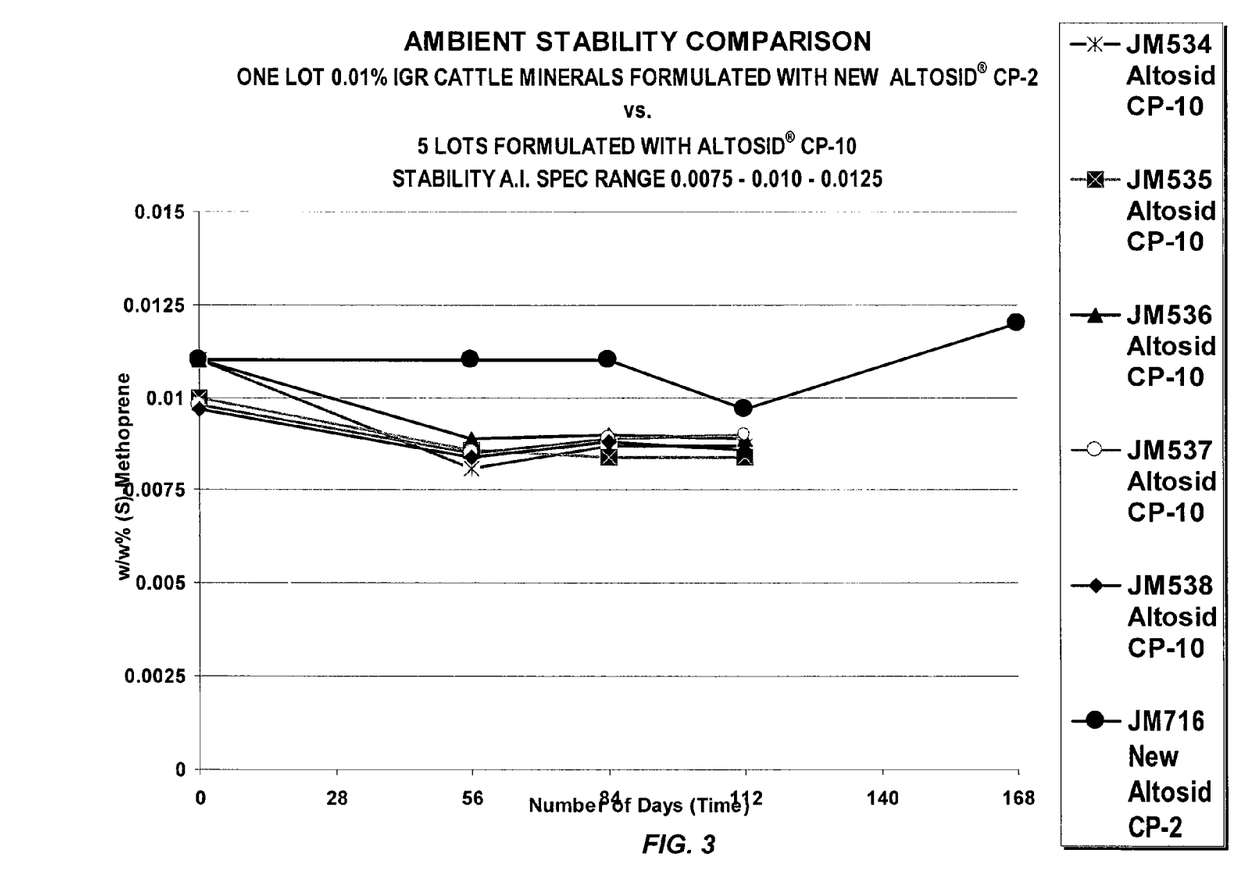
FIG. 3 shows shelf-life comparison data of an embodiment of a pesticide formulation of present invention versus other pesticide formulations.
Figure 4:
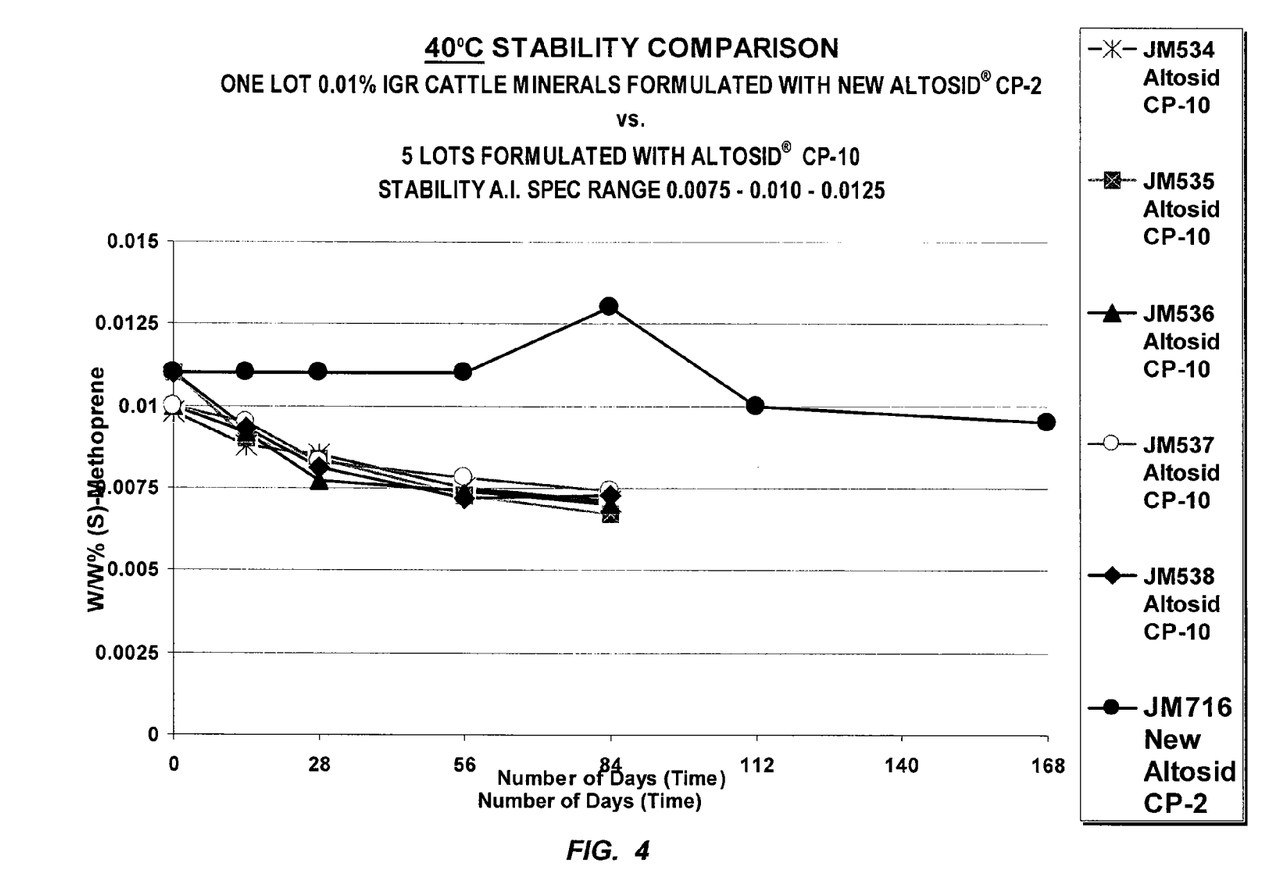
FIG. 4 shows shelf-life comparison data of an embodiment of a pesticide formulation of present invention versus other pesticide formulations.

Storage conditions are compared at ambient temperature and 40° C. and all lots were stored in KRAFT bags with the ends sewn closed. All bags were sampled and the results are in w/w % for (S)-methoprene as a function of time. Each lot was tested at the time interval (0, 14, 28, 56 and 84 days) as indicated using liquid chromatography. The samples were tested at ambient temperature (FIG. 3) as well as at 40° C. (FIG. 4). The lot of the present invention (JM716 Altosid® CP-2) is superior in chemical stability and physical stability.

Altosid® CP-10 composition is 10.5% of the active ingredient (S)-Methoprene applied onto a solid carrier, plus non-hazardous inert ingredients to create a very fine dusty product. Altosid® CP-2 composition is 2% of the active ingredient (S)-Methoprene applied onto dried molasses (saccharides/carbohydrates), plus non-hazardous inert ingredients to create a non-dusty, flow-able, granular product. In this case, the ratio of the molasses to methoprene is 35:1 w/w. As such, Altosid® CP-10 is lacking the saccharide/carbohydrate that Altosid® CP-2 contains.

TABLE I

| Ambient | 0 | 56 | 84 | 112 | 84 | 112 | 168 |
|---|---|---|---|---|---|---|---|
| JM534 Altosid CP-10 | 0.011 | 0.0081 | 0.0087 | 0.0087 | | | |
| JM535 Altosid CP-10 | 0.010 | 0.0086 | 0.0084 | 0.0084 | | | |
| JM536 Altosid CP-10 | 0.011 | 0.0089 | 0.0090 | 0.0089 | | | |
| JM537 Altosid CP-10 | 0.0098 | 0.0085 | 0.0089 | 0.0090 | | | |
| JM538 Altosid CP-10 | 0.0097 | 0.0084 | 0.0088 | 0.0086 | | | |
| JM716 Altosid CP-2 | 0.011 | 0.011 | 0.011 | 0.0097 | 0.011 | 0.0097 | 0.012 |

| 40° C. | 0 | 14 | 28 | 56 | 84 | 112 | 168 |
|---|---|---|---|---|---|---|---|
| JM534 Altosid CP-10 | 0.0098 | 0.0088 | 0.0085 | 0.0075 | 0.0071 | | |
| JM535 Altosid CP-10 | 0.011 | 0.0090 | 0.0084 | 0.0073 | 0.0067 | | |
| JM536 Altosid CP-10 | 0.010 | 0.0092 | 0.0077 | 0.0074 | 0.0070 | | |
| JM537 Altosid CP-10 | 0.010 | 0.0095 | 0.0083 | 0.0078 | 0.0074 | | |
| JM538 Altosid CP-10 | 0.011 | 0.0093 | 0.0081 | 0.0072 | 0.0073 | | |
| JM716 Altosid CP-2 | 0.011 | 0.011 | 0.011 | 0.011 | 0.013 | 0.010 | 0.0095 |

2. Example 2

This example illustrates a 8-week storage stability study for three lots (JM 705, JM706, and JM707) of 0.01% IGR minerals formulated with Altosid® Concentrate (CP-10) compared to one lot of 0.01% IGR mineral formulated with CP-2 (JM716). Three lots (JM705, JM706 and JM707) do not comprise a shelf-life extending agent. Lot JM716 (Altosid® CP-2) is made in accordance to the present invention and comprises a shelf-life extending agent. Storage conditions for all lots are compared at ambient temperature and 40° C. Lots were stored in KRAFT bags with the ends sewn closed. All bags were sampled and the results are in w/w % for (S)-Methoprene as a function of time.

Figure 5:
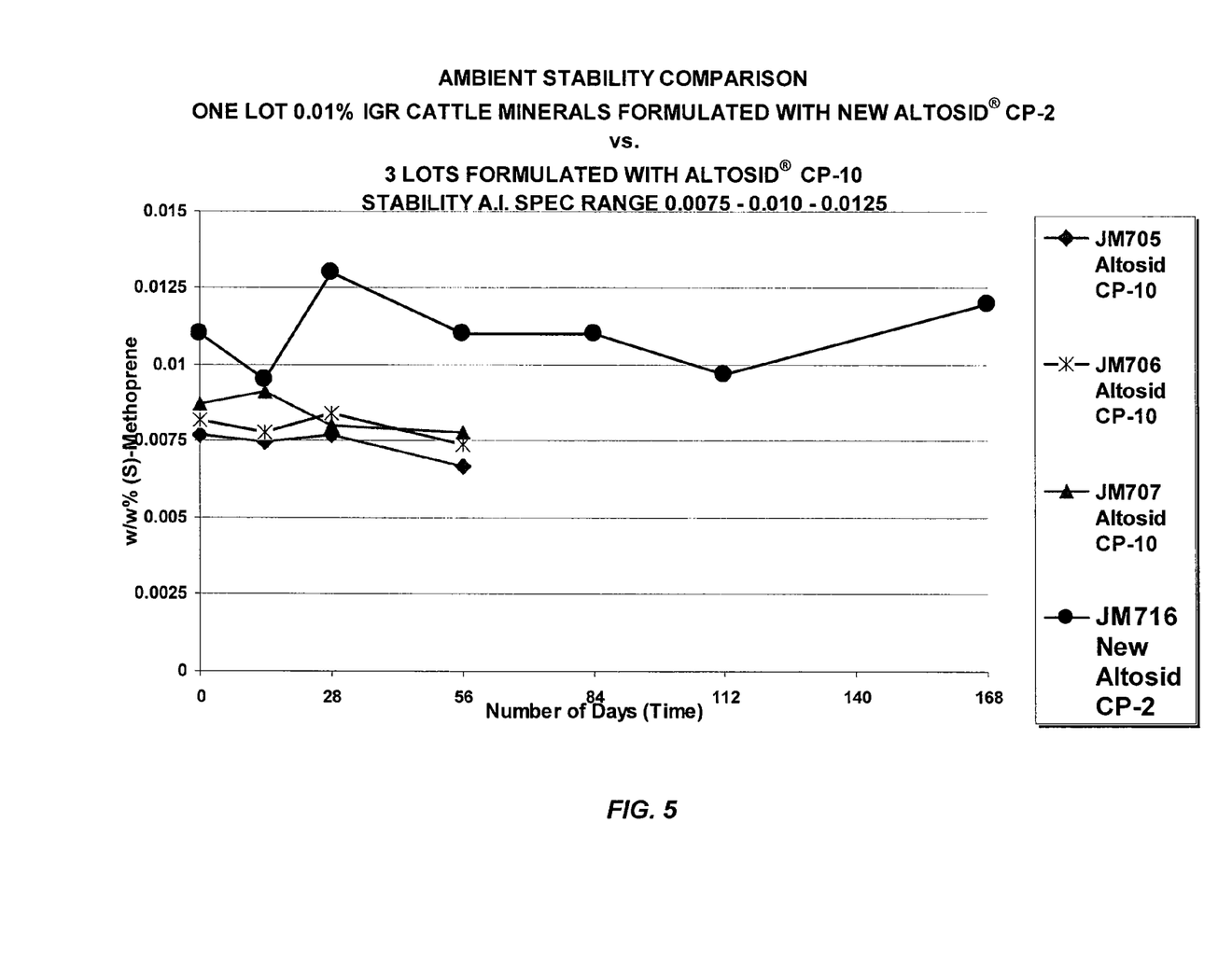
FIG. 5 shows shelf-life comparison data of an embodiment of a pesticide formulation of present invention versus other pesticide formulations.
Figure 6:
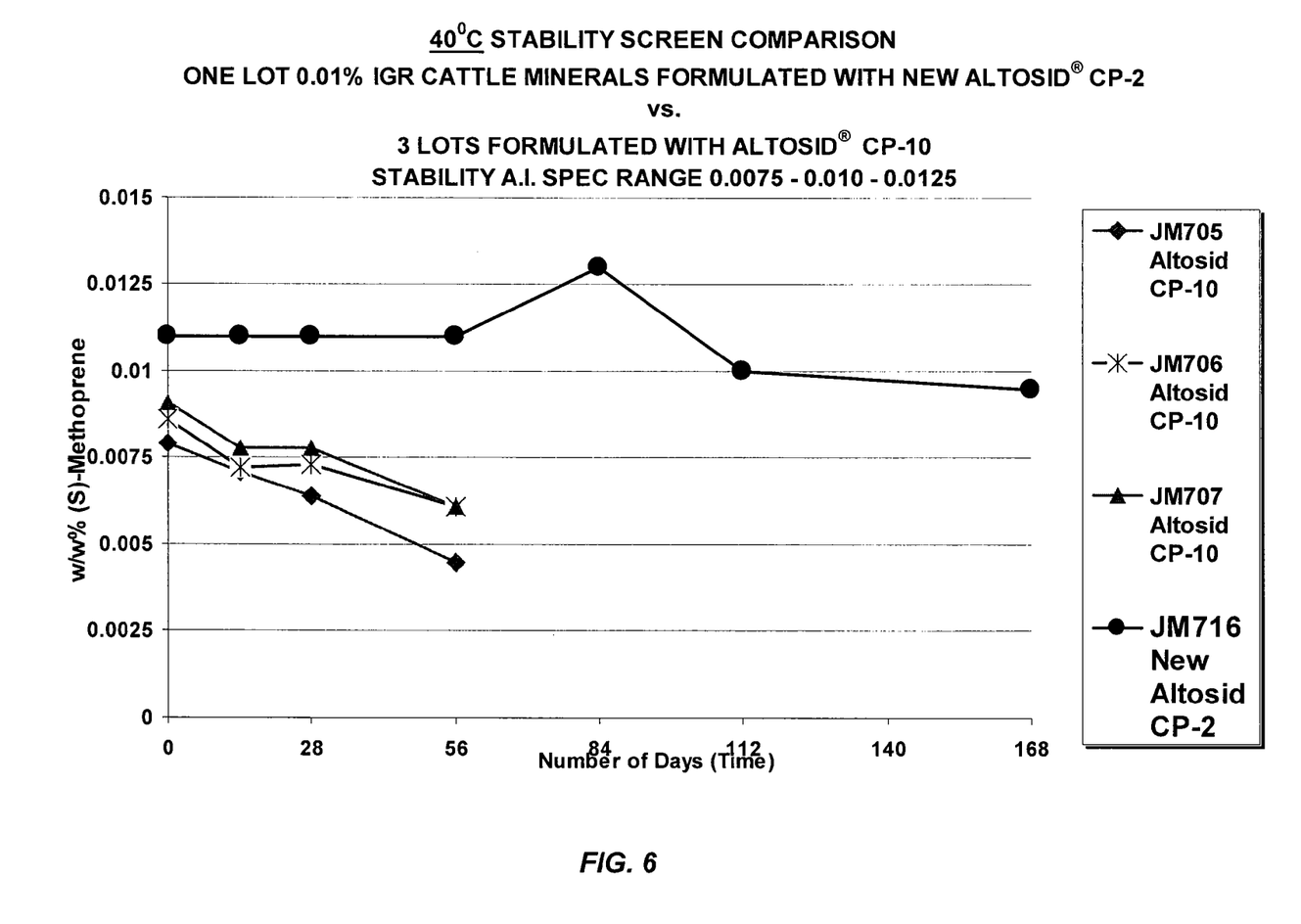
FIG. 6 shows shelf-life comparison data of an embodiment of a pesticide formulation of present invention versus other pesticide formulations.

Each lot was tested at the time interval (0, 14, 28, and 56 days) as indicated using liquid chromatography. The samples were tested at ambient temperature (FIG. 5) as well as at 40° C. (FIG. 6). The lot of the present invention (JM716 Altosid® CP-2) is superior in chemical stability and physical stability.

TABLE 2

| Ambient | 0 | 14 | 28 | 56 | 84 | 112 | 168 |
|---|---|---|---|---|---|---|---|
| JM705 Altosid CP-10 | 0.0077 | 0.0075 | 0.0077 | 0.0067 | | | |
| JM706 Altosid CP-10 | 0.0082 | 0.0078 | 0.0084 | 0.0074 | | | |
| JM707 Altosid CP-10 | 0.0087 | 0.0091 | 0.0080 | 0.0078 | | | |
| JM716 Altosid CP-2 | 0.011 | 0.0095 | 0.013 | 0.011 | 0.011 | 0.0097 | 0.012 |

| 40 C. | 0 | 14 | 28 | 56 | 84 | 112 | 168 |
|---|---|---|---|---|---|---|---|
| JM705 Altosid CP-10 | 0.0079 | 0.0071 | 0.0064 | 0.0045 | | | |
| JM706 Altosid CP-10 | 0.0086 | 0.0072 | 0.0073 | 0.0061 | | | |
| JM707 Altosid CP-10 | 0.0091 | 0.0078 | 0.0078 | 0.0061 | | | |
| JM716 Altosid CP-2 | 0.011 | 0.011 | 0.011 | 0.011 | 0.013 | 0.010 | 0.0095 |

Duplicate samples were assayed and results under each lot are in w/w % for (S)-Methoprene.
All lots were stored in KRAFT bags with the ends sewn closed.

3. Example 3

Figure 7:
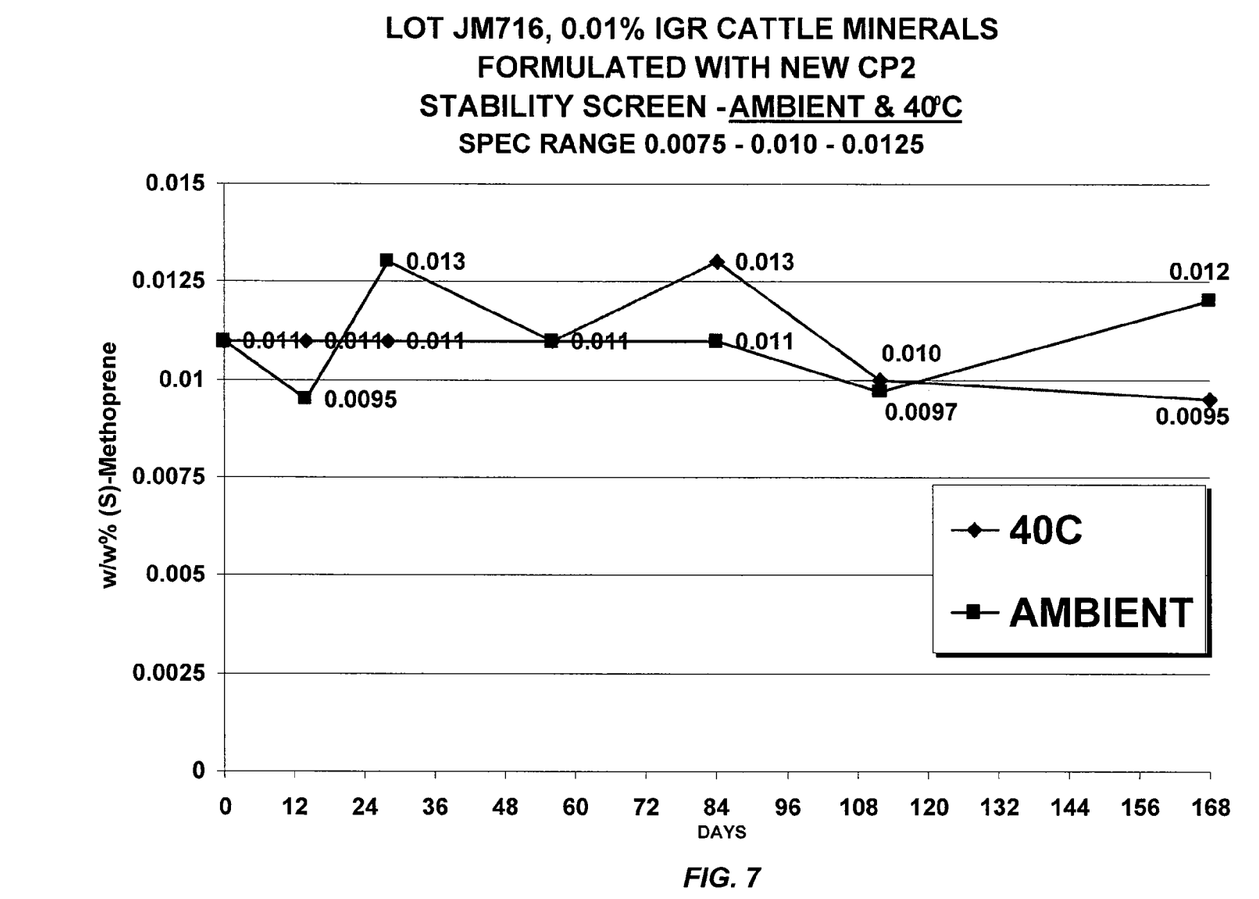
FIG. 7 shows stabilization data of an embodiment of a pesticide formulation of present invention.

This example illustrates the stability of a formulation of the present invention using molasses as the shelf-life extending agent. The lot was tested at the time interval (0, 14, 28, 56, 84, 112, and 168 days) indicated using liquid chromatography. The samples were tested at ambient temperature as well as at 40° C. (FIG. 7). The present invention (JM716 Altosid® CP-2) shows excellent chemical stability and physical stability.

TABLE 3

| | 0 | 14 | 28 | 56 | 84 | 112 | 168 |
|---|---|---|---|---|---|---|---|
| 40° C. | 0.011 | 0.011 | 0.011 | 0.011 | 0.013 | 0.010 | 0.0095 |
| AMBIENT | 0.011 | 0.0095 | 0.013 | 0.011 | 0.011 | 0.0097 | 0.012 |

4. Example 4

The example illustrates a process to make a cattle block of the present invention.

Chemical Blocks and Tubs: Calcium oxide with or without magnesium oxide is used. When CaO reacts with water in the molasses, it binds the ingredients to form a block or tub.

Compressed Blocks: High pressure to compress the materials into blocks is one process for making salt blocks of the present invention. The compressing machine is able to apply pressure from all three directions; top/bottom, left/right and front/back. Binder is preferably used and the most commonly used binders include, for example, cane molasses, cellulose gums (CMC, Methocel, etc), cellulose molasses, lignin sulfonate salts, lignin carboxymethyl ether salts, and other natural gums. The pressure used is usually greater than 1,000 psi.

Cattle Salt Block with Altosid IGR

Formula:

| | |
|---|---|
| Salt (NaCl) | 80.00% |
| Beef Trace Minerals (Micronutrients) Premix | 2.50% |
| Cotton Seed Meal or Soy Bean Meal | 10.00% |
| Calcium Oxide or Carbonate | 1.00% |
| CP10 or CP2 | To provide 25-200 PPM of S-Methoprene |
| Salt (NaCl) | Q.S. 100.00% (Up to 2.5%) |
| Molasses | 4.00% |
| Total | 100.00% W/W |

Figure 8:
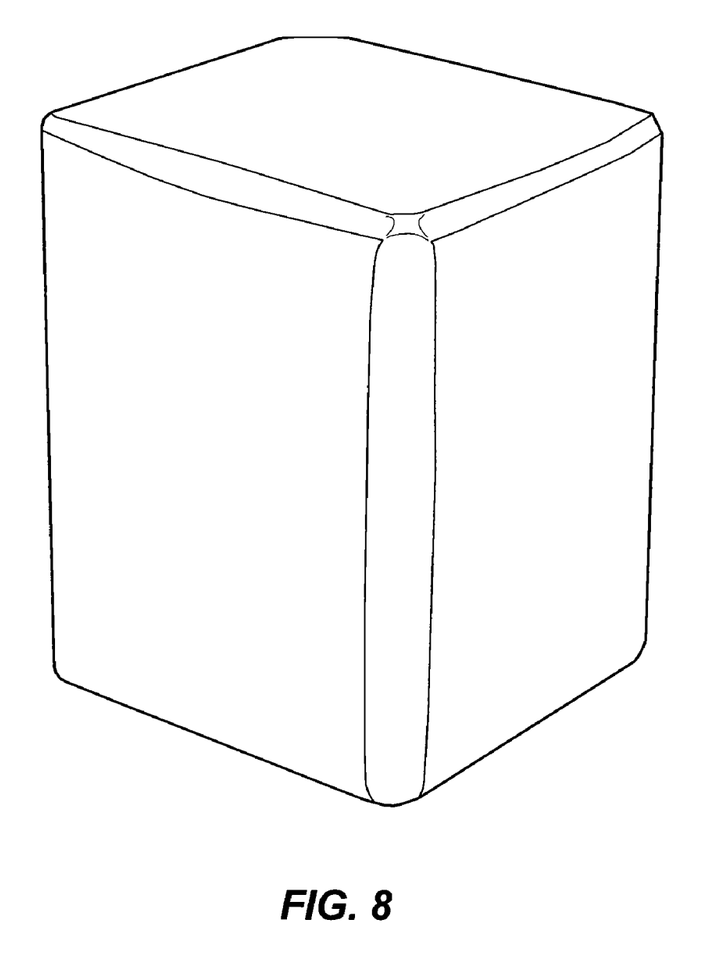
FIG. 8 shows a block embodiment of the of present invention.

Procedure:
1. Mix all the dry ingredients together, when CP10 is used, add CP10 to liquid molasses.
2. While mixing the solid ingredients, pour liquid molasses onto the dry ingredients.
3. Weigh the above mix into the block press and compress into block.
4. Micronutrients or trace mineral premix contains one or more of the following: manganous oxide, zinc oxide, zinc sulfate, ferrous sulfate or carbonate, copper sulfate, ethylene diamine dihydroiodide (EDDI), cobalt carbonate, sodium selenite, etc.
5. In compressed Block formulas, liquid binders such as molasses are used and the percentage of the binder usually ranged from 1% to 10%. FIG. 8 is one illustration of a block of the present invention.

5. Example 5

This example illustrates a process to make a protein cattle block.

High Protein Altosid Block

Formula:

| | |
|---|---|
| Molasses | 25.00% |
| Salt (NaCl) | 25.00% |
| Micronutrients Premix | 1.00% |
| CP10 or CP2 | To provide 25-200 PPM of S-Methoprene |
| Soy Meal | 20.00% |
| Calcium Oxide (CaO) | 15.00% |
| Urea | 10.00% |
| Potassium Phosphate | 3.00% |
| Soy Meal | Q.S. 100.00% |

Procedure:
1. Mix salt, micronutrients premix, soy meal, calcium oxide, urea and potassium phosphate in a suitable mixer.
2. Add appropriate quantity of CP 10 or CP2 to molasses, heat the molasses to 150° F. and pour the hot molasses to the mixture in step 1.
3. Mix the above mixture and wait for the heat generated to subside so that the consistency of the mixture is homogeneous.
4. Pour the mixture into suitable moulds.

6. Example 6

The example illustrates a process to make a cattle block of the present invention.

Cooked Block: Molasses is heated to remove most of the moisture and caramelize the sugars in the molasses. The caramelized sugars are good binders. While heating the molasses or syrup, prepare a glass of cold water. Using a glass rod to pick up some molten molasses and drop it into the cold water to test.

Altosid Mineral Block

Formula:

| | |
|---|---|
| Molasses (90 Brix) | 45.00% |
| Salt (NaCl) | 18.00% |
| Calcium Phosphate or Bone Meal | 10.00% |
| Wheat Bran | 15.00% |
| Micronutrients Premix | 2.00% |
| Macronutrients | 8.00% |
| CP10 or CP2 | To provide 25-200 PPM of S-Methoprene |
| Salt | Q.S. 100.00% |

Figure 9:
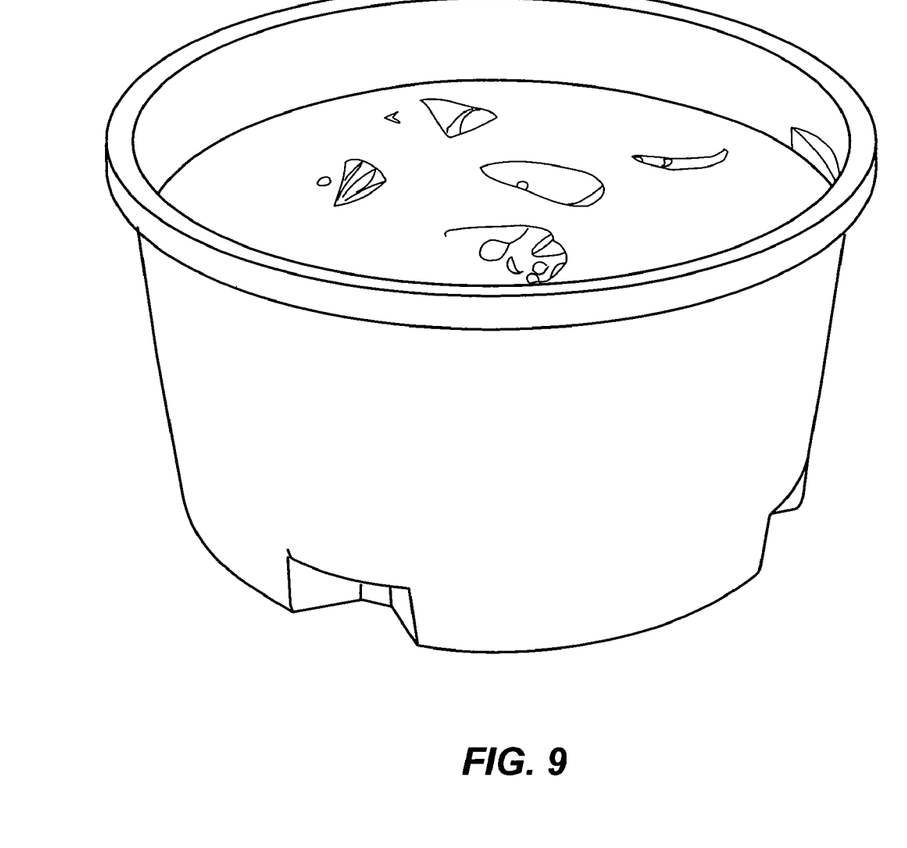
FIG. 9 shows a poured block or tub embodiment of the of present invention.

Procedure:

For pilot or commercial scale, the procedure below is used. It is a continuous process:
1. Mix all the solid ingredients including CP 10 or CP 2 in a suitable mixer.
2. Set the heating equipment at 260° F.-300° F. and start heating molasses. After the molasses is caramelized, allow it to cool to 140° F.-160° F. and mix in the dry ingredients premix.
3. Pour the molten mix into suitable moulds and allow it to cool. FIG. 9 is one illustration of the poured block or tub of the present invention.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A solid shelf-life extending pesticide formulation, said formulation consisting essentially of:
   a) methoprene on a solid carrier, wherein said solid carrier is selected from the group consisting of dry molasses and silica gel;
   b) molasses as a shelf-life extending agent, wherein said solid formulation is formulated as a feed-through animal product wherein the ratio of said molasses to said methoprene is about 100,000:1 w/w to about 500:1 w/w, wherein said final form is about 1 kilogram to 250 kilograms in size;
   c) an antioxidant;
   d) a mineral; and
   e) optionally a protein.

2. The formulation of claim 1, wherein the ratio of said molasses to methoprene in said solid formulation is about 40,000:1 to about 10,000:1 w/w.

3. The formulation of claim 1, wherein the ratio of said molasses to methoprene in said solid formulation is about 5000:1 to about 2000:1 w/w.

4. The formulation of claim 1, wherein the ratio of molasses to methoprene in said solid formulation is about 5000:1.

5. The formulation of claim 1, wherein the ratio of said molasses to said methoprene in said solid formulation is about 2000:1 to about 500:1 w/w.

6. The formulation of claim 1, wherein said antioxidant is selected from the group consisting of Vitamin E, α-tocopherol, α-tocopherol acetate, dl-α-tocopherol acetate, d-α-tocopherol acetate, vitamin A palmitate, propyl gallate, butylated hydroanisole (BHA), butylated hydroxytoluene (BHT), and combinations thereof.

7. The formulation of claim 1, wherein said mineral is one or more members of the group consisting of calcium, phosphorous, salt, potassium, magnesium, zinc, iron, copper, cobalt, iodine, manganese, selenium, and a mixture thereof.

8. The formulation of claim 1, wherein said molasses is a member selected from the group consisting of beet sugar molasses, citrus molasses, hemicellulose extract, dried corn syrup, starch molasses, cane sugar molasses and combinations thereof.

9. The formulation of claim 1, wherein said formulation contains between 0.5 to 10% w/w methoprene.

10. The formulation of claim 1, wherein said formulation contains 2% w/w methoprene.

11. The formulation of claim 1, wherein said formulation contains 0.02% w/w methoprene.

12. The formulation of claim 1, wherein said formulation contains 0.01% w/w methoprene.

13. The formulation of claim 1, wherein said formulation contains 0.0025% methoprene.

14. The formulation of claim 1, wherein shelf-life extending pesticide further consists of a protein.

15. The formulation of claim 1, wherein said final form is about 1 liter to 250 liters in size.

16. The formulation of claim 1, wherein shelf-life extending pesticide is formulated into a final form of a block, poured block or tub.

17. A solid shelf-life extending pesticide formulation, said formulation consisting essentially of:
  a) methoprene on a solid carrier, wherein said solid carrier is selected from the group consisting of dry molasses and silica gel;
  b) molasses as a shelf-life extending agent, wherein said solid formulation is formulated as a feed-through animal product wherein the ratio of said molasses to said methoprene is about 100,000:1 w/w to about 500:1 w/w, wherein said final form is about 1 kilogram to 250 kilograms in size;
  c) a mineral;
  d) optionally an antioxidant; and
  e) optionally a protein.

18. The formulation of claim 17, wherein said molasses is a member selected from the group consisting of beet sugar molasses, citrus molasses, hemicellulose extract, dried corn syrup, starch molasses, cane sugar molasses and combinations thereof.

19. The formulation of claim 17, wherein said formulation contains between 0.5 to 10% w/w methoprene.

20. The formulation of claim 17, wherein said formulation contains 2% w/w methoprene.

21. The formulation of claim 17, wherein said formulation contains 0.02% w/w methoprene.

22. The formulation of claim 17, wherein said formulation contains 0.01% w/w methoprene.

23. The formulation of claim 17, wherein said formulation contains 0.0025% methoprene.

24. The formulation of claim 17, wherein said final form is about 1 liter to 250 liters in size.

25. The formulation of claim 17, wherein said formulation consists further of an antioxidant.

26. The formulation of claim 25, wherein said antioxidant is selected from the group consisting of Vitamin E, α-tocopherol, α-tocopherol acetate, dl-α-tocopherol acetate, d-α-tocopherol acetate, vitamin A palmitate, propyl gallate, butylated hydroanisole (BHA), butylated hydroxytoluene (BHT), and combinations thereof.

27. The formulation of claim 17, wherein said mineral is one or more members of the group consisting of calcium, phosphorous, salt, potassium, magnesium, zinc, iron, copper, cobalt, iodine, manganese, selenium, and a mixture thereof.

28. The formulation of claim 17, wherein said shelf-life extending pesticide further consists of a protein.

29. The formulation of claim 17, wherein shelf-life extending pesticide is formulated into a final form of a block, a cube, poured block or tub.

30. A solid shelf-life extending pesticide formulation, said formulation consisting essentially of:
  a) methoprene on a solid carrier, wherein said solid carrier is selected from the group consisting of dry molasses and silica gel;
  b) molasses as a shelf-life extending agent, wherein said solid formulation is formulated as a feed-through animal product wherein the ratio of said molasses to said methoprene is about 100,000:1 w/w to about 500:1 w/w, wherein said final form is about 1 kilogram to 250 kilograms in size;
  c) a mineral;
  d) a protein; and
  e) optionally an antioxidant.

31. The formulation of claim 30, wherein said molasses is a member selected from the group consisting of beet sugar molasses, citrus molasses, hemicellulose extract, dried corn syrup, starch molasses, cane sugar molasses and combinations thereof.

32. The formulation of claim 30, wherein said formulation contains between 0.5 to 10% w/w methoprene.

33. The formulation of claim 30, wherein said formulation contains 2% w/w methoprene.

34. The formulation of claim 30, wherein said formulation contains 0.02% w/w methoprene.

35. The formulation of claim 30, wherein said formulation contains 0.01% w/w methoprene.

36. The formulation of claim 30, wherein said formulation contains 0.0025% methoprene.

37. The formulation of claim 30, wherein said final form is about 1 liter to 250 liters in size.

38. The formulation of claim 30, wherein said formulation further consists of an antioxidant.

39. The formulation of claim 38, wherein said antioxidant is selected from the group consisting of Vitamin E, α-tocopherol, α-tocopherol acetate, dl-α-tocopherol acetate, d-α-tocopherol acetate, vitamin A palmitate, propyl gallate, butylated hydroanisole (BHA), butylated hydroxytoluene (BHT), and combinations thereof.

40. The formulation of claim 30, wherein said mineral is one or more members of the group consisting of calcium, phosphorous, salt, potassium, magnesium, zinc, iron, copper, cobalt, iodine, manganese, selenium, and a mixture thereof.

41. The formulation of claim 30, wherein shelf-life extending pesticide is formulated into a final form of a block, a cube, poured block or tub.

* * * * *